United States Patent [19]
Brefka et al.

[11] Patent Number: 5,249,568
[45] Date of Patent: Oct. 5, 1993

[54] BODY CAVITY INTRODUCER

[75] Inventors: Paul e Brefka, Southboro, Mass.;
Norman Sohn, Englewood, N.J.;
Evan H. Sohn, New York, N.Y.

[73] Assignee: Logix, Inc., Denville, N.J.

[21] Appl. No.: 724,526

[22] Filed: Jun. 28, 1991

[51] Int. Cl.⁵ ............................................. A61B 1/00
[52] U.S. Cl. ........................................... 128/3; 128/4; 128/7
[58] Field of Search ............... 128/4, 3, 7, 6, 5, 20, 128/17, 18; 606/197; 604/41

[56] References Cited

U.S. PATENT DOCUMENTS

| | | | |
|---|---|---|---|
| 424,140 | 3/1890 | Shuford | 128/17 |
| 1,246,340 | 11/1917 | Smit | 128/6 |
| 3,736,919 | 6/1973 | Cotey | 128/17 |
| 4,167,939 | 9/1979 | Storz | 128/4 |
| 4,690,132 | 9/1987 | Bayer et al. | 128/4 |
| 4,712,536 | 12/1987 | Hawks | 128/3 |
| 4,834,067 | 5/1989 | Block | 128/4 |
| 4,966,130 | 10/1990 | Montaldi | 128/17 |
| 4,972,827 | 11/1990 | Kishi et al. | 128/3 |

FOREIGN PATENT DOCUMENTS

| | | | |
|---|---|---|---|
| 587674 | 1/1959 | Italy | 128/4 |
| 2237202 | 5/1991 | United Kingdom | 128/4 |

Primary Examiner—Richard J. Apley
Assistant Examiner—Karen Ann Jalbert
Attorney, Agent, or Firm—Fish & Richardson

[57] ABSTRACT

An introducer device for receiving a generally bullet-shaped obturator and for facilitating the insertion of an examination instrument into an orifice or body cavity of a patient has first and second hingeably connected half-sections. Each half-section includes a handle, a flange connected to the handle and a nose portion extending continuously from the flange. A connector secures the half-sections together to form a cylindrical hollow nose portion sized to receive and hold the obturator. The generally cylindrical hollow nose portion is large enough in diameter to receive the examination instrument when the obturator is removed.

7 Claims, 1 Drawing Sheet

BODY CAVITY INTRODUCER

This invention relates to a device for introducing a medical instrument (e.g., an endoscope) into a body cavity of a patient for examination purposes.

An endoscope is used to examine the interior of a body cavity or hollow organ of a patient. More particularly, an endoscope is used to visually examine a patient's colon or sigmoid. An endoscope is basically a cylindrical instrument with wires or tubes extending from the end of the cylinder opposite the end inserted into the patient to instrumentation located remote from the patient. The term endoscope, as used, is equivalent to colonoscope or sigmoidoscope. Endoscopy (i.e., colonoscopy or sigmoidoscopy) is a standard diagnostic and therapeutic medical procedure in the fields of gastroenterology, internal medicine, and surgery. It is used to detect and prevent colorectal cancer as well as manage colonic polyps. Endoscopy also is an important diagnostic tool in evaluating patients with abdominal pain, rectal bleeding, diarrhea, constipation, colitis, diverticulitis, and other intestinal disorders.

In a typical procedure, the endoscope is inserted into the rectum of the patient. Because a typical endoscope has a flat end of approximately 11 to 15 millimeters in diameter, the insertion can be painful and/or traumatic to awake, unsedated patients, especially if minor anorectal disorders exist such as fissures, hemorrhoids, or narrowing of the anal canal. In sedated patients the insertion may still be traumatic and cause fissures.

According to the invention, there is an introducer device for receiving a generally bullet-shaped obturator and for facilitating the insertion of a medical examination instrument into an orifice or body cavity of a patient and having first and second hingeably connected half-sections. Each half-section includes a handle, a flange connected to the handle and a nose portion extending continuously from the flange. A connector secures the half-sections together to form a cylindrical hollow nose portion sized to receive and hold the obturator. The generally cylindrical hollow nose portion is large enough in diameter to receive the medical examination instrument when the obturator is removed. Preferably the half-sections are identical and hingeably connected by a living hinge. Preferably the introducer device is made of plastic, such as polypropylene. The introducer is preferably injection-molded, and the obturator is preferably blow-molded. The medical examination instrument is typically an endoscope, colonoscope or sigmoidoscope. According to the process of the invention, insert the obturator into the hollow nose portion of the introducer device, insert the combination of the introducer and the obturator into the cavity of a person, such as the rectum, remove the obturator, leaving the introducer in the body cavity, insert the examination instrument into the hollow nose portion of the introducer, remove the introducer from the body cavity while leaving the examination instrument in the cavity, and opening the introducer along its length and removing it from portions of the examination instrument. Preferably discard the obturator and introducer.

Numerous other features, objects and advantages of the invention will become apparent from the following detailed description when read in connection with the accompanying drawings in which.

Figure 1:
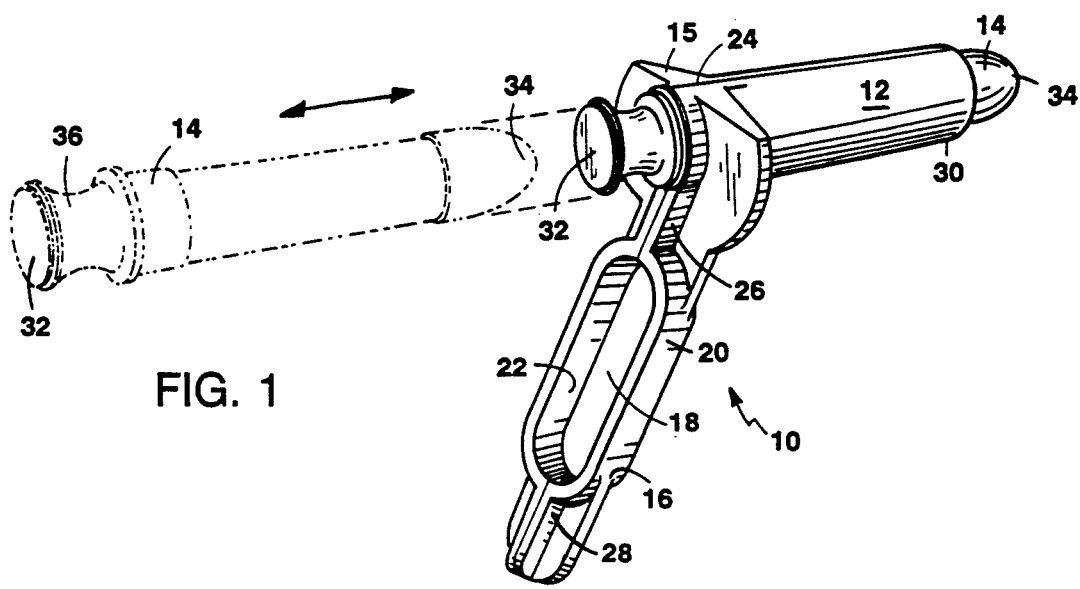
FIG. 1 is a perspective view of the introducer in the closed position including an obturator shown both held in place in the introducer and removed from the introducer.

Referring to FIG. 1, an introducer 10 for facilitating insertion of an endoscope (or, equivalently, a colonoscope or sigmoidoscope) into the rectum of a patient includes a cylindrical hollow nose portion 12 for receiving a bullet-shaped obturator 14. Hollow nose portion 12 of introducer 10 extends continuously from a flange 15. Obturator 14 is shown both in the introducer 10 and removed from the introducer. Introducer 10 also includes a handle 16 with an opening 18 and two sides 20 and 22.

Figure 2:
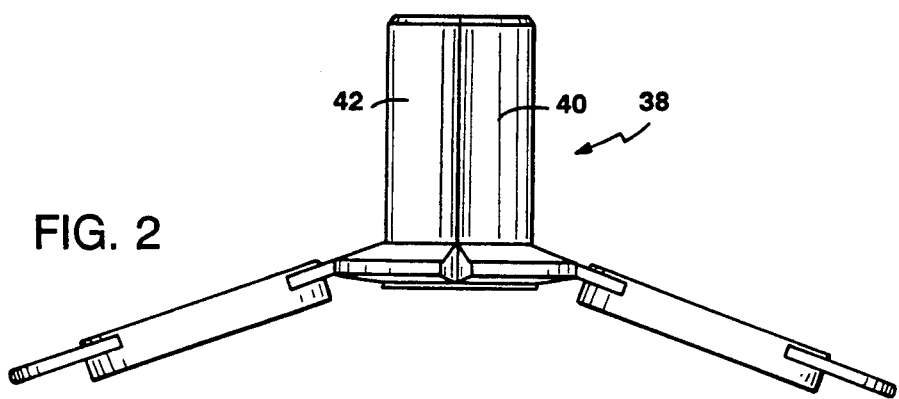
FIG. 2 is a top view of the introducer fully opened.
Figure 3:
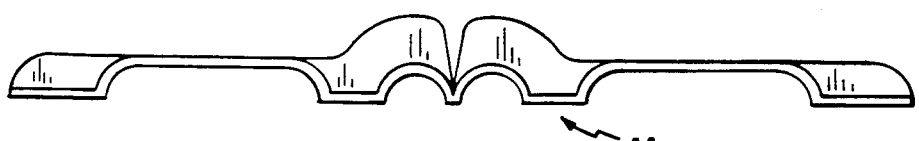
FIGS. 3 and 4 are front views of the introducer fully opened and closed, respectively.

Introducer 10 may be "opened" while outside of the patient by separating or pulling apart the two sides 20 and 22. A living hinge 24 molded along the top edge of the introducer 10 allows the two sides 20 and 22 to pivot away from each other when pulled apart. FIGS. 2 and 3 show introducer 10 in the fully opened position (the obturator is not shown). When introducer 10 is closed (as in FIG. 1) three molded snaps, two 26 and 28 on the handle 16 and one 30 on the nose 12, hold the two sides 20 and 22 securely together.

Having described the structural arrangement of the invention, its mode of operation will be described. Referring to FIG. 1, a practitioner inserts introducer 10 (in the closed position) with bullet-shaped obturator 14 in place into the anus of the patient by grasping handle 16 with a hand so that the hand surrounds sides 20 and 22 and effectively covers opening 18 in handle 16. The thumb engages flat end 32 of obturator 14 to secure the obturator during insertion. The combination of introducer 10 and obturator 14 is then guided into the rectum of the patient with tip 34 of bullet-shaped obturator 14 being the first section to enter the patient followed by nose 12 of introducer 10. The shape of obturator 14 allows atraumatic, painless passage into the rectum through the rectal sphincters. The full depth of insertion is reached when flange 15 of the introducer 10 contacts the exterior of the patient and prevents further penetration.

When obturator 14 and nose 12 of introducer 10 are properly seated in the patient, obturator 14 is withdrawn from hollow nose portion 12 of introducer 10 and discarded while nose 12 of introducer 10 remains inside the patient. The practitioner can easily withdraw obturator 14 by grasping contoured end 36.

With introducer 10 properly in place in the patient and obturator 14 removed, the practitioner inserts the endoscope (not shown) into hollow nose portion 12 of introducer 10 and thus into the patient's rectum to a depth determined by the practitioner.

The practitioner may then remove and discard introducer 10 with the endoscope remaining in the patient's rectum to allow the practitioner to perform the endoscopy.

As indicated above, wires or tubes extend from the end of the endoscope outside the patient to remove instrumentation. These wires or tubes of the endoscope run through and are encircled by hollow nose portion 12 of introducer 10 when introducer 10 is removed from the patient. Introducer 10 may be opened to release the wires or tubes by inserting the fingers of each hand through opening 18 in handle 16, grasping side 20 with one hand and side 22 with the other hand, and pulling sides 20 and 22 apart with enough force to undo the three molded snaps 26, 28, and 30. As stated above, living hinge 24 molded along the top edge of introducer 10 allows sides 20 and 22 to pivot away from each other when pulled apart. With introducer 10 pulled apart (i.e., open), the wires or tubes of the endoscope may be released from hollow nose portion 12 of introducer 10, and introducer 10 may be discarded.

Referring to FIG. 2, introducer 10 is shown in the fully opened position. The outside convex surface 40 of the nose 12 of introducer 10 is shown in the top view of FIG. 2.

Figure 4:
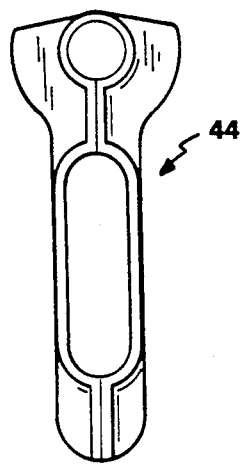

Referring to FIGS. 3 and 4, the introducer 10 is shown in both the fully open and fully closed positions, respectively. Nose 12 of introducer 10 is not visible in the front views of FIGS. 3 and 4.

The introducer according to the invention, which is preferably used once and discarded, is preferably made of Federal Drug Administration (FDA) approved polypropylene and formed by injection molding. The obturator, also preferably used once and discarded, is also preferably made of FDA approved polypropylene but is preferably formed by blow molding. The three molded snaps are integral parts of the introducer and are formed during the injection molding process.

In a specific embodiment, hollow nose portion 12 of introducer 10 is 3 inches long with an inside diameter of 0.69 inches (tolerance of +0.005) and obturator 14 is 4.837 inches long. Handle 16 of introducer 10 is 4.4 inches long. When in place in the introducer, the bullet-shaped end of obturator 14 extends 0.937 inches from the nose of introducer 10 and is 0.69 inches in diameter and the contoured end extends 0.9 inches from the opposite end of the nose and is 0.85 inches in diameter at its widest. The portion of obturator 14 enclosed by the 3-inch long hollow nose portion of introducer 10 has a diameter of 0.57 inches.

Introducers and obturators similar to those described above could be made in various sizes for use with other body cavities and orifices of a patient. Also, introducers and obturators could be molded in various colors to indicate body cavity and/or orifice size.

The invention has a number of advantages. The generally bullet-shaped obturator allows atraumatic and painless passage into a body cavity while reducing the occurrence of fissures. The invention is hygienic and relatively easy and inexpensive to manufacture.

Other embodiments are within the following claims.

What is claimed is:

1. Apparatus comprising a generally bullet-shaped obturator and an introducer device for receiving said generally bullet-shaped obturator and for facilitating the insertion of an examination instrument into an orifice or body cavity of a person, said introducer device comprising,
   first and second hingeably connected half-sections interconnected by a hinge,
   each of said half-sections comprising
   a handle,
   a flange connected to said handle,
   a nose portion extending continuously from said flange and separating said handle from said hinge, and
   a connector for securing said half-sections together to form a cylindrical, hollow nose portion sized to receive and hold said obturator,
   said generally cylindrical, hollow nose portion being large enough in diameter to receive said examination instrument when said obturator is removed.

2. An introducer device in accordance with claim 1 wherein said half-sections are substantially identical.

3. An introducer device in accordance with claim 1 wherein said first and second half-sections are hingeably connected by a living hinge.

4. An introducer device in accordance with claim 1 wherein said introducer device is a unitary structure.

5. An introducer device in accordance with claim 1 wherein said obturator is seated inside said hollow portion.

6. A method for using a generally bullet-shaped obturator and an introducer device having a hollow nose portion openable along a side to facilitate the insertion of an examination instrument into an orifice or body cavity of a person, said introducer device comprising first and second hingeably connected half-sections interconnected by a hinge, each of said half-sections comprising,
   a handle,
   a flange connected to said handle,
   a nose portion extending continuously from said flange and separating said handle from said hinge,
   a connector for securing said half-sections together to form a cylindrical, hollow nose portion sized to receive and hold said obturator,
   said generally cylindrical, hollow nose portion being large enough in diameter to receive said examination instrument when said obturator is removed,
   said method comprising,
   inserting said generally bullet-shaped obturator into said hollow nose portion of said introducer device,
   inserting the combination of said introducer device and the obturator into an orifice or cavity of said person,
   removing the obturator from said person while leaving said introducer device therein,
   inserting the examination instrument into said hollow nose portion of said introducer device,
   removing said introducer device from said person while leaving the examination instrument therein,
   and opening said introducer device along said side and removing said device from surrounding any portions of said examination instrument.

7. A method for using an introducer device in accordance with claim 6 and further including the steps of discarding said obturator and said introducer device.

* * * * *

UNITED STATES PATENT AND TRADEMARK OFFICE
CERTIFICATE OF CORRECTION

PATENT NO.   : 5,249,568

DATED        : 10/05/93

INVENTOR(S)  : Paul e Brefka et al.

It is certified that error appears in the above-identified patent and that said Letters Patent is hereby corrected as shown below:

On the title page: Item [56]

The References cited should also include:

U.S. PATENT DOCUMENTS 2,767,705  10/1956  Moore.........128/4
2,769,441  11/1956  Abramson......128/4
3,720,203   3/1973  Brown.........128/4
4,048,988   9/1977  Regenbogen....128/4
4,776,845  10/1988  Davis.........604/96

FOREIGN PATENT DOCUMENTS 919697      1/1946  France
2708071     2/1977  Germany
US85/01740  9/1985  PCT Signed and Sealed this Twenty-sixth Day of July, 1994

Attest:

BRUCE LEHMAN

Attesting Officer

Commissioner of Patents and Trademarks